United States Patent
Nowakowski et al.

(10) Patent No.: US 7,022,847 B2
(45) Date of Patent: Apr. 4, 2006

(54) METHOD FOR THE PRODUCTION OF 2-(2-ETHOXYPHENYL)-SUBSTITUTED IMIDAZOTRIAZINONES

(75) Inventors: Marc Nowakowski, Wuppertal (DE); Alexander Vetter, Köln (DE)

(73) Assignee: Bayer HealthCare Aktiengesellschaft, Leverkusen (DE)

( * ) Notice: Subject to any disclaimer, the term of this patent is extended or adjusted under 35 U.S.C. 154(b) by 118 days.

(21) Appl. No.: 10/451,706

(22) PCT Filed: Dec. 5, 2001

(86) PCT No.: PCT/EP01/14231

§ 371 (c)(1),
(2), (4) Date: Jan. 5, 2004

(87) PCT Pub. No.: WO02/50075

PCT Pub. Date: Jun. 27, 2002

(65) Prior Publication Data

US 2004/0097505 A1    May 20, 2004

(30) Foreign Application Priority Data

Dec. 18, 2000   (DE)  ................. 100 63 106

(51) Int. Cl.
*C07D 487/04* (2006.01)
(52) U.S. Cl. .................... 544/184; 548/334.1; 564/34
(58) Field of Classification Search ................ 544/183, 544/184

See application file for complete search history.

(56) References Cited

U.S. PATENT DOCUMENTS 4,278,673 A   7/1981   Hartley et al. ............... 424/249
6,362,178 B1  3/2002   Niewohner et al. ......... 514/218

OTHER PUBLICATIONS

Encyclopedia of Organic Reagents for Organic Synthesis, Bromine, and Iodine, John Wiley, 2003.*

* cited by examiner

*Primary Examiner*—Venkataraman Balasubramanian
(74) *Attorney, Agent, or Firm*—Susan Pellegrino

(57) ABSTRACT

The invention relates to a method for the production of 2-phenyl-substituted imidazotriazinones of general formula (I), comprising the reaction of compounds of formula (II) with compounds of formula (III) and subsequent reaction with iodine or bromine, then with a metal cyanide and reaction with an acid.

10 Claims, No Drawings

METHOD FOR THE PRODUCTION OF 2-(2-ETHOXYPHENYL)-SUBSTITUTED IMIDAZOTRIAZINONES

The present invention relates to a process for preparing 2-(2-ethoxyphenyl)-substituted imidazotriazinones.

It is known that compounds able to inhibit cyclic guanosine 3',5'-monophosphate-metabolizing phosphodiesterases (cGMP PDEs) can be employed for the treatment of impotence (compare, for example, EP-B-0 702 555; K. Murray, Drugs, News & Perspectives 6 (1993), 150).

WO 99/24433 describes sulphonamide-substituted imidazotriazinones as potent inhibitors of either one or a plurality of the cyclic guanosine 3',5'-monophosphate-metabolizing phosphodiesterases (cGMP PDEs). In accordance with the nomenclature of Beavo and Reifsnyder (Trends in Pharmacol. Sci. 11, 150–155, 1990), these cGMP PDEs are the phosphodiesterase isoenzymes PDE-I, PDE-II and PDE-V.

The sulphonamide-substituted imidazotriazinones described in WO 99/24433 are prepared from corresponding 2-ethoxyphenyl-substituted imidazotriazinones by reaction with chlorosulphonic acid and subsequent reaction with an appropriate amine. The 2-ethoxyphenyl-substituted imidazotriazinones required as intermediates for this are prepared, according to WO 99/24433, by reacting a compound of the formula (1)

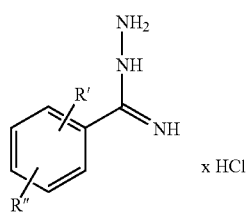

in which
R' and R" are identical or different and represent hydrogen, straight-chain or branched alkyl having up to 6 carbon atoms, hydroxyl or represent straight-chain or branched alkoxy having up to 6 carbon atoms, with a compound of the formula (2)

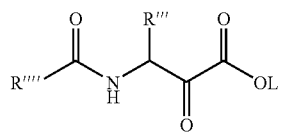

in which
R''' represents hydrogen or straight-chain or branched alkyl having up to 4 carbon atoms,
R'''' represents straight-chain alkyl, having up to 4 carbon atoms,
L represents straight-chain or branched alkyl having up to 4 carbon atoms.

The compounds of the formula (1) are obtained in this case by a three-stage synthesis from the corresponding benzonitriles. The compounds of the formula (2) are prepared in two stages from the corresponding alkylcarbonyl halides and α-amino acids.

It is necessary in this process to proceed via reactive intermediates, which means that implementation of this synthesis on the industrial scale may prove to be difficult.

It was therefore the object of the present invention to provide a process for preparing 2-(2-ethoxyphenyl)-substituted imidazotriazinones which makes it possible for production to take place easily on the industrial scale through avoidance of reactive intermediates.

This object is achieved according to the present invention by a process according to claim 1.

In detail, the process according to the invention for preparing compounds of the formula (I)

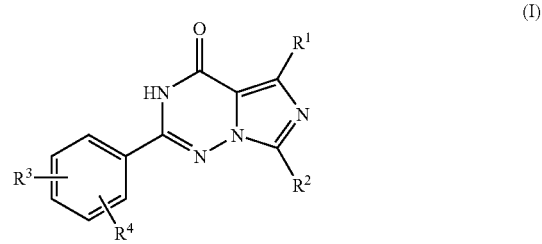

in which
$R^1$ represents hydrogen or straight-chain or branched alkyl having up to 4 carbon atoms,
$R^2$ represents straight-chain alkyl having up to 4 carbon atoms,
$R^3$ and $R^4$ are identical or different and represent hydrogen, straight-chain or branched alkyl having up to 6 carbon atoms, hydroxyl or represent straight-chain or branched alkoxy having up to 6 carbon atoms, comprises reaction of compounds of the formula (II)

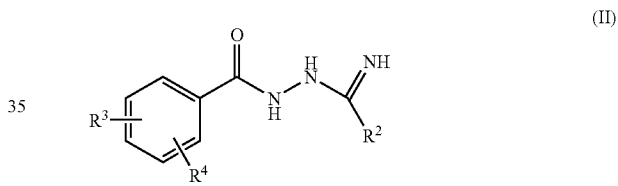

in which $R^2$, $R^3$ and $R^4$ have the meaning indicated above, with compounds of the formula (III)

in which
$R^1$ has the meaning indicated above,
X represents halogen;

in the presence of a base and, where appropriate, of a metal iodide in an organic solvent to give compounds of the formula (IV)

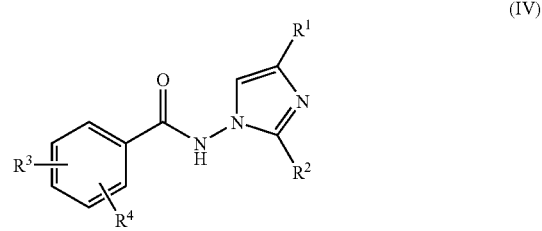

in which $R^1$, $R^2$, $R^3$ and $R^4$ have the meaning indicated above, and subsequent reaction

[A] with iodine in the presence of a base in a solvent, subsequent reaction with a metal cyanide in a solvent and reaction with an acid or

[B] with bromine in acidic medium, subsequent reaction with a metal cyanide in a solvent and reaction with an acid.

According to a preferred embodiment of the present invention, the meanings in the reactants and the final product of the process according to the invention are $R^1$ straight-chain alkyl having up to 4 carbon atoms, $R^2$ for straight-chain alkyl having up to 4 carbon atoms, $R^3$ and $R^4$ identically or differently from one another hydrogen or straight-chain or branched alkoxy having up to 4 carbon atoms.

According to a particularly preferred embodiment of the present invention, the meanings in the reactants and the final product of the process according to the invention are $R^1$ methyl or ethyl, $R^2$ n-propyl, $R^3$ hydrogen $R^4$ ethoxy.

Within the framework of the present invention, unless otherwise indicated, the substituents generally have the following meaning:

Alkyl generally represents a straight-chain or branched hydrocarbon radical having 1 to 6 carbon atoms. Examples which may be mentioned are methyl, ethyl, propyl, isopropyl, butyl, isobutyl, pentyl, isopentyl, hexyl, isohexyl.

Alkoxy generally represents a straight-chain or branched hydrocarbon radical which is bonded via an oxygen atom and has 1 to 6 carbon atoms. Examples which may be mentioned are methoxy, ethoxy, propoxy, isopropoxy, butoxy, isobutoxy, pentoxy isopentoxy, hexoxy, isohexoxy. The terms "alkoxy" and "alkyloxy" are used synonymously.

Halogen represents within the framework of the invention fluorine, chlorine, bromine and iodine.

The compounds of the formula (II) can be prepared according to the present invention by reacting compounds of the formula (V)

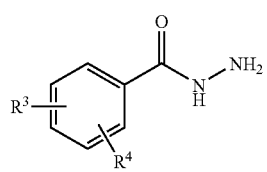

(V)

in which $R^3$ and $R^4$ have the meanings indicated above, with compounds of the formula (VI)

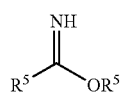

(VI)

in which $R^2$ has the meaning indicated above, $R^5$ represents $C_{1-6}$-alkyl, in an organic solvent in the presence of a base.

The compounds of the formula (V) can be prepared from the corresponding benzoic esters by reaction with hydrazine hydrate by methods known to a skilled person (compare J. March, Advanced Organic Chemistry, 3rd ed., Wiley, 1985, p. 375). The benzoic esters are known or can be prepared by methods familiar to a skilled person.

The compounds of the formula (VI) can be prepared from the corresponding alkyl nitriles, which can be purchased, in a known manner by reaction with HCl and an alcohol (Pinner reaction).

The reaction of the compounds of the formula (V) with compounds of the formula (VI) to give compounds of the formula (II) is carried out in an organic solvent in the presence of a base, for example an organic base such as an amine, preferably triethylamine, preferably under atmospheric pressure and—after mixing the reactants with cooling to, for example, –20° C. to +5° C., preferably 0° C.—stirring the reaction solution for several hours, for example 2 to 60 hours, preferably 24 to 50 hours, at room temperature and subsequent conversion into the hydrochloride for the isolation by dropwise addition of hydrochloric acid with cooling to, for example, –20° C. to +5° C., preferably 0° C. The reactants can in this case, depending on their characteristics, be employed in equimolar amounts, or one of the reactants is employed in an up to three-fold excess.

Solvents suitable for this reaction are the conventional organic solvents which are not changed under the reaction conditions. These preferably include alcohols such as methanol, ethanol or isopropanol, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is likewise possible to use mixtures of the solvents mentioned. Isopropanol is particularly preferred.

The reaction is generally carried out under atmospheric pressure. However, it is also possible to operate under elevated pressure or reduced pressure (for example in a range from 0.5 to 5 bar).

The reaction of the compounds of the formula (II) with compounds of the formula (III) to give the compounds of the formula (IV) can take place in two ways according to the invention.

On the one hand, the reaction can be carried out in such a way that the compounds of the formula (II) are reacted in the form of the corresponding free base (obtainable from the hydrochloride of the compounds of the formula (II) by reaction with a base such as an alkali metal or alkaline earth metal base, preferably an alkali metal or alkaline earth metal carbonate such as sodium bicarbonate) with compounds of the formula (III) in an organic solvent in the presence of a base and, where appropriate, of a metal iodide, preferably under atmospheric pressure and stirring the reaction solution for several hours, for example 2 to 12 hours, preferably 3 to 6 hours, at elevated temperature, for example 30 to 80° C., preferably 40 to 60° C., in particular 50° C., to give the compounds of the formula (IV). The reactants can in this case, depending on their characteristics, be employed in equimolar amounts, or the compound of the formula (III) is employed in an up to three-fold excess.

The compounds of the formula (III) can either be purchased or obtained in a manner known to the skilled person by an α-halogenation reaction of the corresponding aldehydes or ketones, which can be purchased (compare J. March, Advanced Organic Chemistry, 3rd ed., Wiley, 1985, pages 529 et seq.). It is preferred in both variants (the amine variant and the carbonate variant) for the corresponding chloro aldehydes or chloro ketones of the formula (III) to be employed.

Solvents suitable for this reaction are the conventional organic solvents which are not changed under the reaction conditions. These preferably include alcohols such as methanol, ethanol or isopropanol, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is likewise possible to use mixtures of the solvents mentioned. Acetonitrile is particularly preferred.

The reaction is generally carried out under atmospheric pressure. However, it is also possible to operate under elevated pressure or reduced pressure (for example in a range from 0.5 to 5 bar).

Suitable bases are, in particular, cyclic amines such as, for example, piperidine, pyridine, dimethylaminopyridine or $C_1$–$C_4$-alkylamines, such as, for example, triethylamine. Triethylamine is preferred. The base is generally employed in an amount of from 1 mol to 4 mol, preferably in equimolar amount, in each case based on 1 mol of the compound of the formula (II).

All ionic iodides can be employed as metal iodide. Preference is given according to the invention to alkali metal or alkaline earth metal iodides such as, in particular, potassium iodide.

However, division into two steps is also possible, with reaction of the compounds of the formula (II) in the form of the corresponding hydrochloride with compounds of the formula (III) initially in an organic solvent in the presence of a base, preferably under atmospheric pressure and stirring the reaction solution, for, for example, 1 to 30 hours, preferably 12 to 24 hours, at 0 to 25° C., preferably 10 to 20° C., in particular 15° C., and with reaction of the resulting intermediates then in another inert organic solvent at elevated temperature, for example 50 to 200° C., preferably 70 to 150° C., in particular 85 to 115° C., to give the compounds of the formula (IV). The reactants can in this case be employed, depending on their characteristics, in equimolar amounts, or the compound of the formula (III) is employed in an up to threefold excess.

Solvents suitable for this reaction are the conventional organic solvents which are not changed under the reaction conditions. These preferably include alcohols such as methanol, ethanol or isopropanol, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is likewise possible to use mixtures of the solvents mentioned. Particular preference is given to acetone for the first step and to xylene for the second step.

The reaction is generally carried out under atmospheric pressure. However, it is also possible to operate under elevated pressure or reduced pressure (for example in a range from 0.5 to 5 bar).

Suitable bases are in general alkali metal or alkaline earth metal carbonates such as, in particular, potassium carbonate. The base is generally employed in an amount of from 1 mol to 4 mol, preferably in an amount of 2 mol, in each case based on 1 mol of the compound of the formula (II).

The compounds of the formula (IV) obtained in this way can be converted according to the invention into the compounds according to the invention of the formula (I) by two routes, these routes differing from one another only in the first step.

The first step in both routes consists of a halogenation of position 5 in the imidazole ring. In the first route, this halogenation takes place by reacting the compounds of the formula (IV) with iodine in the presence of a base in a solvent, preferably under atmospheric pressure and stirring the reaction solution for, for example, 1 to 48 hours, preferably 12 to 36 hours, in particular 24 hours, at room temperature with exclusion of light. The iodine is in this case preferably employed in excess, for example a two- to four-fold excess.

Solvents suitable for this reaction are the solvents customary for halogenation reactions which are not changed under the reaction conditions. These preferably include alcohols such as methanol, ethanol or isopropanol, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine or water. It is likewise possible to use mixtures of the solvents mentioned. A dioxane/water mixture is particularly preferred according to the invention.

The reaction is generally carried out under atmospheric pressure. However, it is also possible to operate under elevated pressure or reduced pressure (for example in a range from 0.5 to 5 bar).

Suitable bases are in general alkali metal or alkaline earth metal carbonates such as, in particular, sodium carbonate. The base is generally employed in an amount of from 1 mol to 10 mol, preferably in an amount of from 2 mol to 6 mol, in each case based on 1 mol of the compound of the formula (IV).

In the second route, this halogenation takes place by reacting the compounds of the formula (IV) with bromine in acidic medium, preferably under atmospheric pressure and stirring the reaction solution for, for example, 1 to 24 hours, preferably 1 to 12 hours, in particular 1 to 6 hours, at room temperature. The bromine in this case is preferably employed in excess, for example an up to two-fold excess.

The reaction is generally carried out under atmospheric pressure. However, it is also possible to operate under elevated pressure or reduced pressure (for example in a range from 0.5 to 5 bar).

Acids which can be employed are weak organic carboxylic acids such as, for example, alkanecarboxylic acids, in particular acetic acid, which do not undergo any unwanted side reactions with the compounds of the formula (IV).

The iodine or bromine compounds obtained in this way are subsequently reacted with a metal cyanide in a solvent preferably under atmospheric pressure and stirring the reaction solution for several hours, for example 2 to 12 hours, preferably 3 to 6 hours, at elevated temperature, for example 30 to 120° C., preferably 60 to 110° C., in particular 100° C., to give the corresponding nitriles.

Solvents suitable for this reaction are the organic solvents customary for such reactions which are not changed under the reaction conditions. These preferably include alcohols such as methanol, ethanol or isopropanol, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformrnamide, hexamethylphosphoramide, acetonitrile, acetone, dimethoxyethane or pyridine or water. It is likewise possible to use mixtures of the solvents mentioned. Pyridine is particularly preferred.

The reaction is generally carried out under atmospheric pressure. However, it is also possible to operate under elevated pressure or reduced pressure (for example in a range from 0.5 to 5 bar).

Metal cyanides which can be used are the usual metal cyanides employed for introducing a nitrile function. The use of CuCN is preferred according to the invention. The metal cyanide is generally employed in an amount of from 2 mol to 10 mol, preferably in an amount of from 2 mol to 8 mol, in each case based on 1 mol of the corresponding iodine or bromine compound.

In the case where the corresponding bromine compound is used, it is appropriate, depending on the characteristics of this compound, additionally to add a metal iodide. All ionic iodides can be employed as metal iodide. Alkali metal or alkaline earth metal iodides such as, in particular, potassium iodide are preferred according to the invention. The metal iodide is preferably added in less than the stoichiometric amount, for example in catalytic amounts such as half the stoichiometric amount in each case based on 1 mol of the bromine compound employed.

It is possible to obtain from the nitrile compounds obtained in this way the compounds according to the invention of the formula (I) in the last step by partial hydrolysis of the nitrile function to the corresponding amide function and subsequent intramolecular ring formation. This reaction can be carried out by methods known to the skilled person (compare J. March, Advanced Organic Chemistry, 3rd ed., Wiley, 1985, p. 788.). Preferred according to the invention is reaction with a mineral acid such as sulphuric acid with cooling to, for example, −20° C. to +5° C., preferably 0° C., and stirring the reaction solution for several hours, for example 2 to 12 hours, preferably 3 to 6 hours, initially at room temperature and subsequently at elevated temperature, for example 30 to 120° C., preferably 60 to 110° C., in particular 70° C.

The reaction is generally carried out under atmospheric pressure. However, it is also possible to operate under elevated or reduced pressure (for example in a range from 0.5 to 5 bar).

The compounds according to the invention are intermediates for the synthesis of certain inhibitors of cGMP-metabolizing PDEs which are described in WO 99/24433. These cGMP PDE inhibitors can be prepared from the compounds according to the invention of the formula (I) for example as described in WO 99/24433.

The present invention is described in more detail hereinafter by means of non-limiting preferred examples and comparative examples. Unless indicated otherwise, all stated amounts refer to percentages by weight.

EXAMPLES $^1$H-NMR spectra were recorded using a Bruker WP-200 SY spectrometer at room temperature. The solvent used was deuterated dimethyl sulphoxide or deuterochloroform with tetramethylsilane as internal standard (unless noted otherwise).

MS spectra were recorded using the AMD M 40 and PE/SCIEX API 150 spectrometers. The relative signal intensity is indicated (in per cent relative to the base peak).

HPLC analysis was recorded with the Hewlett Packard HP 1050 using a Phenomenex column of the type Prodigy ODS III. The eluent used for the starting compounds (Examples A, C and D) was a mixture of acetonitrile and 10 mM neutral phosphate buffer (pH 7.2). An eluent mixture of methanol and 10 mM acidic phosphate buffer (pH 2.4) was used for the other compounds.

Starting Compounds

Example A

Preparation of 2-ethoxybenzohydrazide

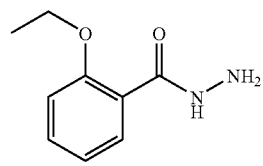

Ethyl 2-ethoxybenzoate (100 g, 128.7 mmol) and hydrazine hydrate (100%, 25 ml, 128.7 mmol) are dissolved in 200 ml of ethanol and heated under reflux for 5 hours. A further 12.5 ml (64.3 mmol) of hydrazine hydrate are added and the reaction mixture is heated under reflux for a further 7 hours. For working up, the reaction mixture is extensively concentrated and then stirred with 300 ml of cyclohexane at room temperature. After cooling to 0° C., the crystals are filtered off with suction, washed twice with 50 ml of cold cyclohexane each time and finally dried in a vacuum oven at 35° C. and 300 mbar overnight.

Yield: 72.5 g $^1$H-NMR: δ=1.4 (t, 3 H), 4.2 (q, 2 H), 4.6 (NH$_2$, 2 H), 7.0–7.7 (Ar, 4 H), 9.1 (CONH, 1 H)

MS: 361 (2M+H, 15), 181 (M+H, 100)

HPLC: 96 area %

Example B

Preparation of ethyl butyrimidate hydrochloride

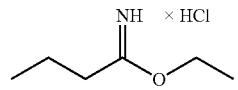

Butyronitrile (85 ml, 839 mmol) is dissolved in absolute ethanol (65 ml, 961 mmol) and cooled to 0° C. to 5° C.

While cooling further, gaseous hydrogen chloride (about 40 g, about 1.1 mol, differential weighing of the pressure cylinder) is passed into the solution. The reaction mixture is left at about 4° C. for 96 hours and then, while stirring, 260 ml of diisopropyl ether are added, and the mixture is cooled to −20° C. and filtered with suction at 0° C. through a sintered funnel. The crystals are rapidly (the product is hygroscopic) washed twice with 50 ml of cold diisopropyl ether each time and stored, sealed air-tight, in a refrigerator.

Yield: 131.6 g $^1$H-NMR: δ=0.9 (t, 3 H), 1.3 (t, 3 H), 1.6 (m, 2 H), 2.6 (t, 2 H), 4.5 (q, 2 H), 11.3+12.2 (NH, 1 H)

MS: 115 (M+, 10), 10 (20), 87 (22), 72 (25), 70 (22), 59 (50), 43 (100), 41 (40), 36 (22)

Example C

Preparation of N'-(1-iminobutyl)-2-ethoxybenzohydrazide hydrochloride

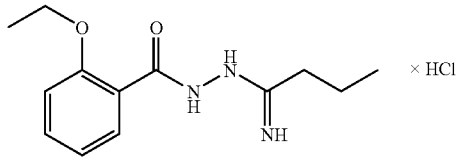

Ethyl butyrimidate hydrochloride from Example B (71.5 g, 472 mmol) is introduced into triethylamine (65 ml, 472 mmol) and cooled to 0° C. 2-Ethoxybenzohydrazide from Example A (85 g, 472 mmol) is suspended in 250 ml of isopropanol and added to the ethyl butyrimidate mixture. The reaction mixture is stirred at room temperature for 48 hours, the solid (triethylamine hydrochloride) is removed, and 25% strength hydrochloric acid (150 ml, 1.18 mol) is slowly added dropwise to the mother liquor at 0° C. to 5° C. The suspension of crystals is then stirred at 0° C. to 5° C. for 1 hour and the crystals are filtered with suction through a sintered funnel, washed with 100 ml of cold isopropanol and dried in a vacuum oven at 30° C. and 300 mbar overnight.

Yield: 96.4 g $^1$H-NMR: δ=1.0 (t, 3 H), 1.4 (t, 3 H), 1.8 (m, 2 H), 2.6 (t, 2 H), 4.2 (q, 2 H), 7.0–7.9 (Ar, 4 H), 9.0+10.0+11.8 (NH, 2 H), 10.4 (CONH, 1 H)

MS: 499 (2M+H, 20), 250 (M+H, 100)

HPLC: 86 area %

Example D

Preparation of 2-ethoxy-N-(4-methyl-2-propylimidazol-1-yl)benzamide

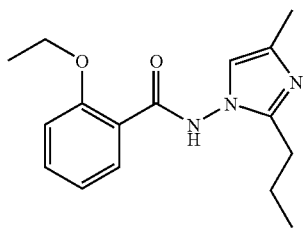

Amine Variant

N'-(1-Iminobutyl)-2-ethoxybenzohydrazide from Example C (5 g, 17.5 mmol) is taken up in 100 ml of saturated sodium bicarbonate solution and then extracted twice with 100 ml of dichloromethane. The phases are separated, and the organic phase is dried, completely evaporated and taken up in 300 ml of acetonitrile. In a separate flask, chloroacetone (3.0 ml, 35 mmol), triethylamine (5.5 ml, 17.5 mmol) and potassium iodide (2.9 g, 17.5 mmol) are introduced into 15 ml of acetonitrile and heated to 50° C. The solution of N'-(1-iminobutyl)-2-ethoxybenzohydrazide in acetonitrile prepared above is added over the course of about 1 hour to the above mixture at 50° C., and the mixture is kept at 50° C. for 4 hours. The resulting suspension is cooled to room temperature, the solid is removed, and the filtrate is completely concentrated and taken up in 200 ml of dichloromethane. The dichloromethane solution is washed twice with 200 ml of saturated sodium chloride solution each time. The organic phase is dried with sodium sulphate and concentrated in a rotary evaporator.

Yield: 3.7 g

The spectroscopic data were identical to the product prepared by the carbonate variant.

Carbonate Variant

N'-(1-Iminobutyl)-2-ethoxybenzohydrazide from Example C (200 g, 700 mmol), potassium carbonate (193.5 g, 1400 mmol) and potassium iodide (23.2 g, 140 mmol) are introduced into 1400 ml of acetone at 15° C. and then stirred at 15° C. until conversion is complete (about 20 hours). 1400 ml of water are added, and the acetone is removed by distillation in vacuo. The suspension is cooled, and the crystals are isolated and washed. The crystals obtained in this way are resuspended in 600 ml of xylene (mixture of isomers), and water is removed by distillation at 85 to 115° C. in vacuo. The resulting solution is cooled, and the product is crystallized by seeding and adding cyclohexane. The crystals are isolated, washed with cyclohexane and dried in vacuo.

Yield: 144.9 g $^1$H-NMR: δ=0.9 (t, 3 H), 1.4 (t, 3 H), 1.6 (m, 2 H), 2.1 (s, 3 H), 2.5 (t, 2 H), 4.2 (q, 2 H), 6.8 (1H, imidazole), 7.0–7.6 (Ar, 4 H), 11.1 (CONH, 1 H)

MS: 575 (2M+H, 15), 451 (10), 288 (M+H, 100)

HPLC: 94 area %

PREPARATION EXAMPLES

Example 1

2-(2-Ethoxyphenyl)-5-methyl-7-propyl-3H-imidazo[5.1-f]-triazin-4 one (by Iodination Route)

1a) 2-Ethoxy-N-(5-iodo-4-methyl-2-propylimidazol-1-yl)benzamide

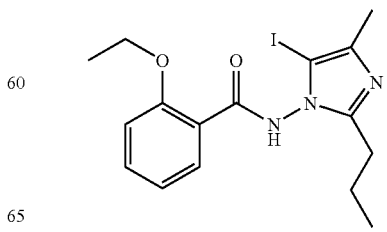

2-Ethoxy-N-(4-methyl-2-propylimidazol-1-yl)benzamide from Example D (3.5 g, 12.2 mmol) is dissolved in 480 ml of a dioxane/water mixture, and sodium carbonate (3.9 g, 36.6 mmol) and iodine (6.8 g, 26.8 mmol) are added. The mixture is stirred with exclusion of light at room temperature for 24 hours. 50 ml of ethyl acetate are added to the reaction mixture and washed twice with 50 ml of saturated sodium sulphite solution each time. The combined aqueous phases are re-extracted twice with 50 ml of ethyl acetate each time, and the combined organic phase is dried with sodium sulphate and concentrated in a rotary evaporator.

Yield: 4.1 g $^1$H-NMR: δ=0.9 (t, 3 H), 1.4 (t, 3 H), 1.6 (m, 2 H), 2.1 (s, 3 H), 2.6 (t, 2 H), 4.2 (q, 2 H), 7.1–7.6 (Ar, 4 H), 11.1 (CONH, 1 H)

MS: 414 (M+H, 100), 222 (10), 149 (30), 121 (65)

HPLC: 82 area %

1b) N-(5-Cyano-4-methyl-2-propylimidazol-1-yl)-2-ethoxybenzamide

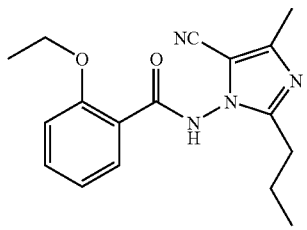

2-Ethoxy-N-(5-iodo-4-methyl-2-propylimidazol-1-yl)benzamide from Example 1a (0.5 g, 1.2 mmol) and copper(I) cyanide (0.7 g, 7.5 mmol) are introduced into 10 ml of pyridine and heated at 100° C. for three hours. The reaction mixture is cooled to room temperature, 50 ml of dichloromethane are added, and the solid is removed by filtration. The filtrate is washed three times with 50 ml of water each time, and the organic phase is re-extracted with 50 ml of dichloromethane. The combined organic phase is dried with sodium sulphate and concentrated. To remove the remaining pyridine, the residue is taken up in 50 ml of dichloromethane and washed six times with 100 ml of water each time. The organic phase is dried with sodium sulphate and concentrated in a rotary evaporator. The residue is finally mixed with 100 ml of toluene and concentrated.

Yield: 0.3 g $^1$H-NMR: δ=0.9 (t, 3 H), 1.4 (t, 3 H), 1.7 (m, 2 H), 2.3 (s, 3 H), 2.6 (t, 2 H), 4.2 (q, 2 H), 7.1–7.7 (Ar, 4 H), 11.5 (CONH, 1 H)

MS: 313 (M+H, 100), 149 (25), 149 (30), 120 (15)

HPLC: 82 area %

1c) 2-(2-Ethoxyphenyl)-5-methyl-7-propyl-3H-imidazo[5,1-f]triazin-4-one

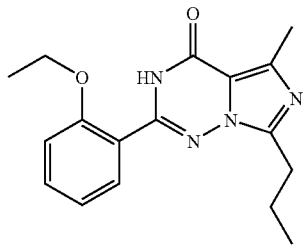

48.5% strength sulphuric acid (5 ml) is cooled to 0° C., and N-(5-cyano-4-methyl-2-propylimidazol-1-yl)-2-ethoxybenzamide from Example 1(0.2 g, 0.6 mmol) is added. The suspension is stirred at room temperature for 2 hours and then at 70° C. for 1 hour. The mixture is diluted with 30 ml of water and extracted three times with 30 ml of dichloromethane each time. The combined organic phase is dried with sodium sulphate and concentrated.

Yield: 0.1 g $^1$H-NMR: δ=1.0 (t, 3 H), 1.6 (t, 3 H), 1.9 (m, 2 H), 2.8 (s, 3 H), 3.3 (t, 2 H), 4.3 (q, 2 H), 7.0–8.2 (Ar, 4 H), 10.3 (CONH, 1 H)

MS: 313 (M+H, 100), 149 (25), 151 (40), 121 (15)

HPLC: 80 area %

Example 2

2-(2-Ethoxyphenyl)-5-methyl-7-propyl-3H-imidazo[5,1-f]-triazin-4 one (by Bromination Route)

2a) N-(5-Bromo-4-methyl-2-propylimidazol-1-yl)-2-ethoxybenzamide

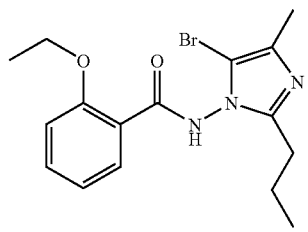

2-Ethoxy-N-(4-methyl-2-propylimidazol-1-yl)benzamide from Example D (50 g, 174 mmol) is introduced into acetic acid. Bromine (12.5 ml, 243.6 mmol) dissolved in acetic acid is added dropwise at room temperature. The mixture is then stirred at room temperature until conversion is complete (up to 3 hours). For working up, water and ethanol (or optionally acetone) are added to the mixture. The product is precipitated by neutralizing with sodium hydroxide solution. The crystals are isolated, washed and dried in vacuo.

Yield: 59.7 g $^1$H-NMR: δ=0.9 (t, 3 H), 1.4 (t, 3 H), 1.65 (m, 2 H), 2.1 (s, 3 H), 2.55 ( t, 2 H), 4.2 (q, 2 H), 7.1–7.7 (Ar, 4 H), 11.2 (CONH, 1 H)

MS: 366 (M+H, 100), 203 (30), 149 (20), 121 (30)

HPLC: 99 area %

2b) N-(5-Cyano-4-methyl-2-propylimidazol-1-yl)-2-ethoxybenzamide

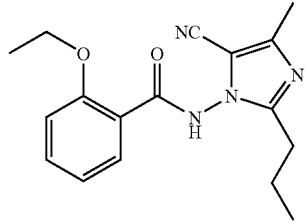

N-(5-Bromo-4-methyl-2-propylimidazol-1-yl)-2-ethoxybenzamide from Example 2a (0.5 g, 1.2 mmol) and copper(I) cyanide (0.3 g, 3.5 mmol) are introduced into 12.5 ml of pyridine and heated at 100° C. for 6 hours. Potassium iodide (23 mg, 0.56 mmol) is added to the mixture, which is then stirred for a further 6 hours at 100° C. The reaction mixture is cooled to room temperature and, after addition of 50 ml of ethyl acetate, washed with dilute alkaline $H_2O_2$ solution. The aqueous phase is re-extracted with ethyl acetate, and the combined ethyl acetate phase is concentrated, finally azeotroped with toluene and again concentrated.

Yield: 0.3 g $^1$H-NMR: δ=0.9 (t, 3 H), 1.4 (t, 3 H), 1.7 (m, 2 H), 2.3 (s, 3 H), 2.6 (t, 2 H), 4.2 (q, 2 H), 7.1–7.7 (Ar, 4 H), 11.5 (CONH, 1 H)

MS: 313 (M+H, 100), 149 (25), 149 (30), 120 (15)

HPLC: 82 area %

2c) 2-(2-Ethoxyphenyl)-5-methyl-7-propyl-3H-imidazo[5,1-f]triazin-4-one

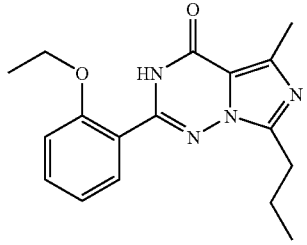

48.5% strength sulphuric acid (5 ml) is cooled to 0° C., and N-(5-cyano-4-methyl2-propylimidazol-1-yl)-2-ethoxybenzamide from Example 2b (0.2 g, 0.6 mmol) is added. The suspension is stirred at room temperature for 2 hours and then at 70° C. for 1 hour. The mixture is diluted with 30 ml of water and extracted three times with 30 ml of dichloromethane each time. The combined organic phase is dried with sodium sulphate and concentrated.

Yield: 0.1 g $^1$H-NMR: δ=1.0 (t, 3 H), 1.6 (t, 3 H), 1.9 (m, 2 H), 2.8 (s, 3 H), 3.3 (t, 2 H), 4.3 (q, 2 H), 7.0–8.2 (Ar, 4 H), 10.3 (CONH, 1 H)

MS: 313 (M+H, 100), 149 (25), 151 (40), 121 (15)

HPLC: 80 area %

The invention claimed is:

1. Process for preparing a compound of the formula (I)

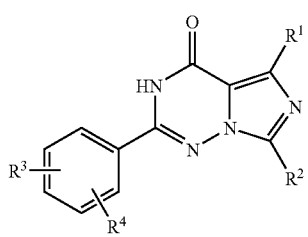

(I)

in which
R$^1$ represents hydrogen or straight-chain or branched alkyl having up to 4 carbon atoms,
R$^2$ represents straight-chain alkyl having up to 4 carbon atoms,
R$^3$ and R$^4$ are identical or different and represent hydrogen, straight-chain or branched alkyl having up to 6 carbon atoms, or represent straight-chain or branched alkoxy having up to 6 carbon atoms,
comprising reaction of a compound of the formula (II)

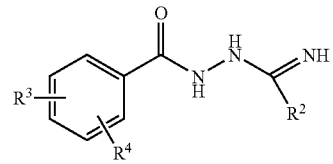

(II)

in which R$^2$, R$^3$ and R$^4$ have the meaning indicated above, with a compound of the formula (III)

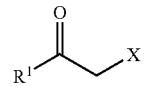

(III)

in which
R$^1$ has the meaning indicated above,
X represents halogen;
in the presence of a base and, where appropriate, of a metal iodide in an organic solvent to give a compound of the formula (IV)

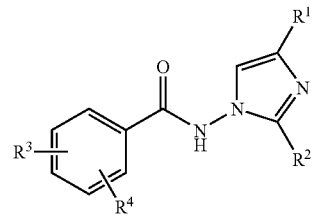

(IV)

in which R$^1$, R$^2$, R$^3$ and R$^4$ have the meaning indicated above, and subsequent reaction

[A] with iodine in the presence of a base in a solvent, subsequent reaction with a metal cyanide in a solvent and reaction with an acid or

[B] with bromine in acidic medium, subsequent reaction with a metal cyanide in a solvent and reaction with an acid.

2. Process according to claim 1, characterized in that R$^1$ denotes straight-chain alkyl having up to 4 carbon atoms,
R$^2$ denotes straight-chain alkyl baiting up to 4 carbon atoms,
R$^3$ and R$^4$ denote, identically or differently from one another, hydrogen or straight-chain or branched alkoxy having up to 4 carbon atoms.

3. Process according to claim 1, characterized in that R$^1$ denotes methyl or ethyl,
R$^2$ denotes n-propyl,
R$^3$ denotes hydrogen,
R$^4$ denotes ethoxy.

4. Process according to claim 1, characterized in that X in the compound of the formula (III) represents chlorine.

5. Process according to claim 1, characterized in that the reaction of the compounds of the formula (II) and (III) is carried out in the presence of potassium iodide and triethylamine.

6. Process according to claim 1, characterized in that the reaction of the compounds of the formula (II) and (III) is carried out in the presence of potassium carbonate.

7. Process according to claim 1, characterized in that the reaction of a compound of the formula (IV) with iodine is carried out with the exclusion of light in the presence of sodium carbonate and subsequently with CuCN in pyridine.

8. Process according to claim 1, characterized in that the reaction of a compound of the formula (IV) with bromine is carried out in the presence of acetic acid and subsequently with CuCN in pyridine in the presence of potassium iodide.

9. Process according to claim 1, characterized in that sulphuric acid is used as the acid in the concluding step.

10. Process according to claim 1, characterized in that a compound of the formula (II) is prepared by reacting a compound of the formula (V)

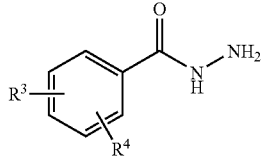

(V)

in which

R$^1$ and R$^4$ have the meaning indicated in claim 1, with a compound of the formula (VI)

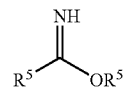

(VI)

in which

R$^2$ has the meaning indicated in claim 1,

R$^5$ represents C$_{1-6}$-alkyl, in an organic solvent in the presence of a base.

* * * * *